Feb. 2, 1971 G. MERRILL Plant Pat. 3,022
PEACH TREE
Filed Jan. 22, 1969
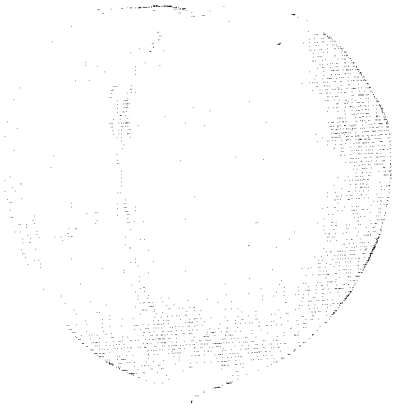
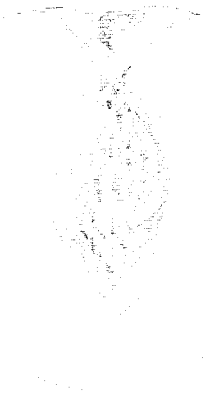
GRANT MERRILL
INVENTOR
Virgil L. Gerard
ATTORNEY

United States Patent Office

Plant Pat. 3,022
Patented Feb. 2, 1971

3,022

PEACH TREE

Grant Merrill, 416 N. Anderson Road,
Exeter, Calif. 93221

Filed Jan. 22, 1969, Ser. No. 793,198
Int. Cl. A01h *5/03*
U.S. Cl. Plt.—43 1 Claim The present invention relates to a peach tree and more particularly to a new and distinct variety thereof broadly characterized by its vigorous growth and its regular bearing habits, and by its fruit which is large, with a red blush over about half of the surface, and has firm flesh which remains firm while the fruit is on the tree so only one or two pickings are needed, but which softens a few days after being picked into a meaty to melting flesh which completely parts from the stone in many fruits when ripened under these conditions.

The instant variety, June Lady (0–46A), most nearly resembles the Harmony variety of peach (U.S. Plant Pat. No. 2,152) but is an improvement thereon in that it ripens about a week earlier, has more red in its skin color, and remains firm longer on the tree.

I originated the present variety near Red Bluff, Tehama County, Calif., by crossing Fortyniner (unpatented) with Gemfree (U.S. Plant Patent 1,409). One of the resulting seedlings was then asexially reproduced in the San Joaquin Valley of California where its characteristics proved identical to those of the original tree and worthy of commercial use.

The accompanying drawing is an oil painting of a characteristic fruit of the subject variety showing its outside shape and skin color and, by means of the division of a second characteristic fruit on its suture plane, its flesh coloration, stone coloration, and freedom of the flesh from the stone.

Referring more specifically to the promological characteristics of this new and distinct variety of peach tree, the following has been observed under the ecological conditions prevailing neax Exeter, Tulare County, Calif., and is an outlined description thereof. All major color plate identifications are by reference to Maerz and Paul, Dictionary of Color, 1st ed.

TREE

Generally: medium size, medium vigorous, vase shaped when pruned, medium dense.
Productivity: moderate with regular sets of fruit.
Trunk: straight, medium stocky, shaggy, gray.
Main branches: straight with some bending, gray on older branches, brown on younger branches.
Lenticels: medium in quantity, medium size.
Twigs: medium size, medium internode length, green on current seasons growth, brown on older growth.
Leaves: location from center stalk of terminal branches 30 to 36 inches long; size, generally medium, 3¾ to 7¾ inches long, ¾ to 1¾ inches wide; medium thickness; lanceolate; tip, accuminate; color, upper surface dark green, lower surface lighter green; veins very light yellowish green; class (Meader & Blake: Proceedings of the American Society for Horticultural Science, vol. 37, p. 203), 3 on larger leaves, 2 on smaller leaves; margin, crenate, glandular; petiole, medium size; glands, reniform, 1 to 5 in number, medium size, alternate yellow green, located at base of leaf and on petiole; stipules, present on new leaves dropping off early.

FLOWER BUDS

Medium size, plump, pubescent, free.

FLOWERS

Early, about with July Elbertas (U.S. Plant Pat. No. 15); small; pink with salmon tinge; pollen abundant.

FRUIT

Maturity (when described): firm ripe June 22, 1968.
Size: generally large for that season; diameter, axially 2⅜ to 2¾ inches, transverse in suture plane 2⅝ to 3 inches, right angle to suture plane 2⅝ to 2⅞ inches.
Shape: generally cordate to nearly globose with tip acuminate.
Suture: shallow depression; extends from base to near apex but discontinues at apex; has slight depression beyond pistil dorsal surface; rounded.
Cavity: abrupt; elongated in suture plane showing on both sides; depth ¼ to ½ inch; breadth ½ to ¾ inch; markings, yellow with red blush where exposed to sun.
Base: retuse.
Apex: mucronate; pistil point apical, very short.
Stem: length, ¼ to ⅜ inch; diameter, ⅛ inch; frequently adheres to stone.
Skin: medium thick, medium tough, sweet, tenacious to flesh; color, light yellow 9–L–1 to darker yellow 9–L–9 with red blush from light red 1–G–11 to medium red 1–K–11 to darker red 6–L–6; pubescence, scant.
Flesh: color light yellow 9–J–1 to medium yellow 9–K–5 with some light red around the stone; amygdalin moderate; juice moderate to abundant; texture, firm and meaty; fibers, fine, moderate in quantity; ripens evenly; flavor, mild delicate vinuous; firmness, good, uniform, and persistent while fruit remains on tree; aroma, distinct; eating quality, best.
Stone: completely free when fruit is picked firm ripe and further ripened off the tree, semi-free when fruit is ripened on the tree, cling when hard ripe; fibers, few and short; size, medium 1⅜ to 1¾ inches long, 1 to 1⅛ inches wide, ¾ to ⅞ inch thick; form, obovate; base, straight to oblique; hilum, oval; apex, acuminate; sides unequal, flattened on one side; surface irregularly furrowed near base and near apex; pitted toward base, pits elongated; ventral edge, thick with a few small grooves, and with large grooves on each side dorsal edge, deep groove toward base extending about half way to apex; color, when first removed from the fruit, light brown 11–D–7 to medium brown 13–E–10 to dark brown 8–H–12 in grooves and pits.
Eating quality: good.
Shipping quality: excellent.

Although the new variety of peach possesses the described characteristics under the growing conditions near Exeter, Tulare County, Calif., having first been observed near Red Bluff, Tehama County, Calif., it is to be understood that variations of the usual magnitude in the characteristics incident to the growing conditions, fertilization, pruning, and pest control are to be expected.

Having thus described and illustrated my new variety of peach tree, what is claimed is:

1. A new and distinct variety of peach substantially as illustrated and described, which is characterized by the vigorous growth and regular bearing habits of the tree; and by its fruit which is large for its season, and has a red blush over half of its surface and firm flesh which remains firm on the tree so only one or two pickings are neecssary but which soften a few days after picking, and which is then completely free from the stone in most fruit; and which most nearly resembles Harmony (U.S. Plant Pat. No. 2,152) but is distinguished therefrom in that it ripens about one week earlier, has more red in its skin color, and remains firm longer on the tree.

No references cited.

ROBERT E. BAGWILL, Primary Examiner